US00PP09430P

United States Patent [19]

Poulsen

[11] Patent Number: Plant 9,430

[45] Date of Patent: Jan. 16, 1996

[54] ELATIOR BEGONIA PLANT NAMED 'SANNE'

[76] Inventor: Jens N. Poulsen, Gartneriet J.N.P., Larsmindevej 1, Lisbjerg, DK-8200 Aarhus N., Denmark

[21] Appl. No.: 385,871

[22] Filed: Feb. 9, 1995

[51] Int. Cl.[6] ..... A01H 5/00

[52] U.S. Cl. ..... Plt./87.18

[58] Field of Search ..... Plt./87.17, 87.18

*Primary Examiner*—James R. Feyrer

*Attorney, Agent, or Firm*—Proprietary Rights Intl.

[57] ABSTRACT

A distinctive cultivar of Elatior Begonia plant named Sanne, characterized by its upright and spreading growth habit; compact plant size; freely branching habit; strong stems and stem base; small leaves; soft red flower color; large number of flowers per raceme; small flowers; early and even flowering; and strong and vigorous root system.

1 Drawing Sheet

The present invention relates to a new and distinctive cultivar of Begonia plant, botanically known as *Begonia* × *hiemalis,* commercially known as Elatior Begonia, and referred to by the cultivar name Sanne.

The new cultivar was discovered by the inventor in Aarhus, Denmark, as a mutation of the nonpatented Elatior begonia cultivar Kathleen, and was observed in a group of 15-cm flowering plants of the parent.

Asexual reproduction of the new cultivar by tip cuttings in Aarhus, Denmark, has shown that the unique features of this new Elatior Begonia are stabilized and are reproduced true to type in successive propagations.

The new cultivar has not been observed under all possible environmental conditions. The phenotype may vary significantly with variations in environment such as temperature, light level and daylength, without, however, any variance in genotype.

The following traits have been repeatedly observed and are determined to be the unique characteristics of Sanne. The following characteristics differentiate the new cultivar from the parent cultivar Kathleen and other Elatior Begonias commercially know and used in the floriculture industry, namely the nonpatented cultivar Netja:

1. Plants of the cultivar Sanne are upright and spreading in growth habit. Plants of the cultivars Kathleen and Netja are upright, but not spreading.

2. Plants of the cultivar Sanne are compact. Plants of the cultivar Sanne are less vigorous and shorter than plants of the cultivars Kathleen and Netja.

3. Plants of the cultivar Sanne do not require pinching to produce full plants as they are freely branching. Plants of the cultivar Sanne are more freely branching than plants of the cultivars Kathleen and Netja.

4. Plants of the cultivar Sanne have strong stems and stem bases. Plants of the cultivar Sanne have greater stem and stem base strength than plants of the cultivars Kathleen and Netja.

5. Plants of the cultivar Sanne have small leaves. Plants of the cultivar Sanne have smaller leaves than plants of the cultivars Kathleen and Netja.

6. Flowers of the cultivar Sanne are soft red in color (Red Group 50A/50B). In comparison, flowers of the cultivar Kathleen are coral in color (Red Group 39B), and flowers of the cultivar Netja are dark pink in color (Red Group 52B).

7. Plants of the cultivar Sanne have a large number of flowers per raceme. Plants of the cultivar Sanne have more flowers per raceme than plants of the cultivars Kathleen and Netja.

8. Flowers of the cultivar Sanne are small in diameter. Plants of the cultivar Sanne have smaller flowers than plants of the cultivars Kathleen and Netja.

9. Plants of the cultivar Sanne flower early. Plants of the cultivar Sanne flower earlier than plants of the cultivars Kathleen and Netja.

10. Plants of the cultivar Sanne are evenly covered with flowers. Plants of the cultivar Sanne are more evenly covered with flowers than plants of the cultivars Kathleen and Netja.

11. Plants of the cultivar Sanne have strong and vigorous root systems. Plants of the cultivar Sanne have stronger and more vigorous root systems than plants of the cultivars Kathleen and Netja.

The accompanying colored photograph illustrates the overall appearance and flower color of the new cultivar, showing the colors as true as it is reasonably possible to obtain in colored reproductions of this type. The photograph comprises a side perspective view of a typical potted plant of Sanne.

The following observations, measurements, values, and comparisons describe plants grown in Aarhus, Denmark, under commercial practice in a glass-covered greenhouse with day and night temperatures ranging from 19 to 21C. Depending on cloud cover, light levels ranged from 5,000 to 35,000 lux.

In the following description, color references are made to The Royal Horticultural Society Colour Chart except where general terms of ordinary dictionary significance are used.

Botanical classification: *Begonia* × *hiemalis* cultivar Sanne.

Commercial classification: Elatior Begonia.

Parentage: Naturally-occurring mutation of *Begonia* × *hiemalis* cultivar Kathleen.

Propagation:

A. *Type.*—By tip cuttings.

B. *Time to initiate roots.*—Tip cuttings root in 17 to 21 days at temperatures of 21C.

C. *Rooting habit.*—Root system is very strong and develops rapidly. Roots are prolific and dense. Roots are fine and fibrous in texture.

Plant description:

A. *Plant form.*—Upright and spreading potted plant, freely branching with good stem and stem base strength. Flowers are fully double and abundant. Plants flower continuously under warm (higher than 18 C.) night temperatures.

B. *Growth habit.*—Moderate growth rate and vigor. Compact in plant habit with short internodes. Suitable for 10 to 15-cm containers. Under optimal environmental conditions, 10 to 12 weeks are required to produce proportional 12.5-cm potted plants (approximately 20 cm in height) from tip cuttings that are directly-stuck in the container. Vegetative shoots are formed at basal nodes and flowering shoots are formed at upper nodes.

C. *Foliage and stem description.*—1. Leaf arrangement: Simple, alternate. 2. Quantity of leaves: 20 to 30 per 12.5-cm potted plant. 3. Leaf length: 7 to 8 cm. 4. Leaf width: 9 to 10 cm. 5. Leaf shape: Cordate. 6. Leaf tip: Acute. 7. Leaf base: Obtuse. 8. Leaf margin: Serrate. 9. Leaf texture: a. Upper side: Smooth, leathery, glabrous. b. Under side: Leathery, sparsely pubescent. 10. Leaf color: a. Young foliage, upper side: 132A. b. Young foliage, under side: 139D. c. Mature foliage, upper side: 139A. d. Mature foliage, under side: 139C. 11. Leaf attachment: Stalked. 12. Petiole length: 1.2 to 1.5 cm. 13. Petiole diameter: 4 to 5 mm. 14. Petiole color: 139D. 15. Venation pattern: Palmate, smooth on upper side, raised on under side. 16. Venation color: a. Upper side: 141C. b. Under side: 139D. 17. Stem color: 139B. 18. Stem strength: Very strong. 19. Stem base strength: Very strong.

Flowering description:

A. *Flowering habit.*—Flowers arranged in racemes. Many racemes in flower simultaneously. Flowering continuous under warm (higher than 18 C.) night temperatures.

B. *Natural flowering season.*—Plants will flower year around regardless of daylength, however plants will flower earlier and more abundantly if daylength is 12 hours or less.

C. *Quantity of flowers.*—Six to 8 flowers per raceme, up to 50 flowers at various stages of development may be present per 12.5-cm pot.

D. *Flowers.*—1. Shape: Circular. 2. Diameter; 2.5 to 4 cm. 3. Height: 1.5 to 1.7cm.

E. *Peduncle.*—1. Length: 1 to 1.5 cm. 2. Diameter: 2.5 mm. 3. Color: 147D. 4. Aspect: Erect. 5. Texture: Glabrous.

F. *Flower bud.*—1. Shape: Ovoid. 2. Diameter: 0.5 cm. 3. Length: 0.5 cm. 4. Rate of opening: 3 to 5 days. 5. Color: 49C.

G. *Tepals.*—1. Arrangement: Rosette. 2. Shape: Flat, rounded. 3. Quantity per flower: 8 to 20. 4. Length: 1.5 to 2 cm. 5. Width: 1.5 to 2 cm. 6. Color: a. When opening: 49D. b. Fully open: (1) Upper side: 50A/50B. (2) Under side: 50C. c. Fading to: 50C. 7. Margin: Entire. 8. Texture: Smooth, velvety, glabrous.

H. *Sepals.*—1. Arrangement: Opposite. 2. Shape: Oval. 3. Quantity per flower: 2. 4. Length: 1.5 cm. 5. Width: 1.5 cm. 6. Color: a. Upper side: 146B. b. Under side: 146C. 7. Tip: Rounded, slightly pointed. 8. Margin: Entire. 9. Texture: Thin, transparent.

I. *Reproductive organs.*—1. Stamens: None. 2. Pistils: None:

Postproduction longevity:

A. *Individual flowers.*—Generally 2 to 3 weeks.

B. *Whole plants.*—Generally 6 weeks under interior conditions.

Disease resistance: Plants of the cultivar Sanne are resistant to Powdery Mildew.

I claim:

1. A new and distinct Elatior Begonia plant named Sanne, as illustrated and described.

* * * * *

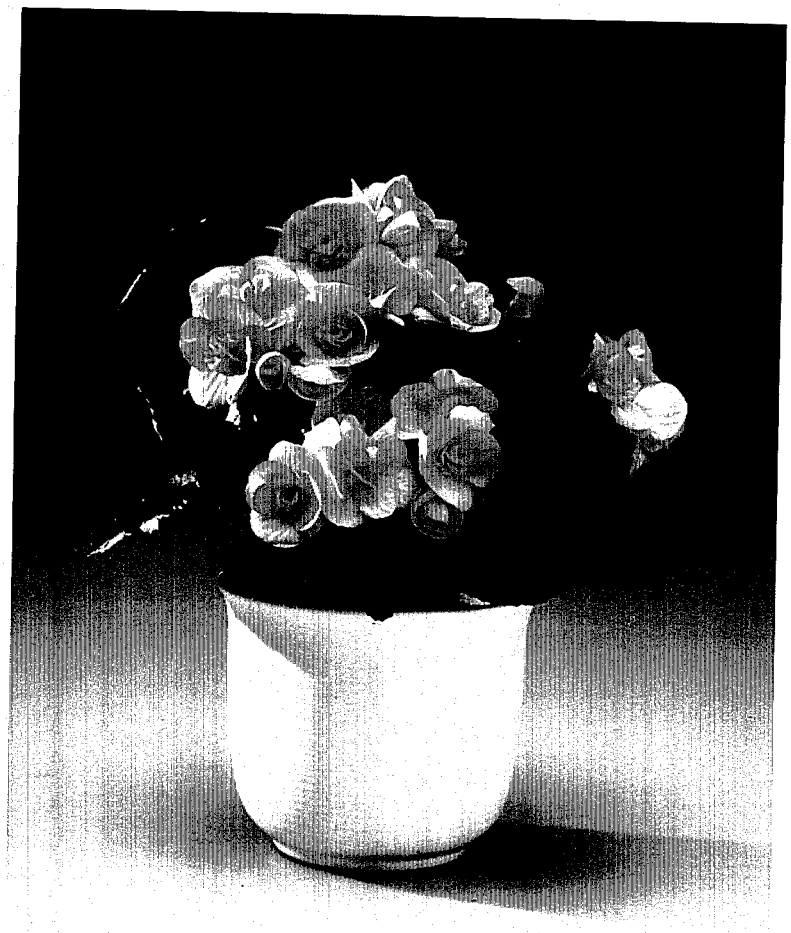
SANNE
[redacted]